(12) United States Patent
Kozaki et al.

(10) Patent No.: US 7,267,974 B2
(45) Date of Patent: Sep. 11, 2007

(54) POLYHYDROXYALKANOATE SYNTHESIZING MICROORGANISM AND PROCESS OF PRODUCING POLYHYDROXYALKANOATE USING THE SAME

(75) Inventors: Shinya Kozaki, Tokyo (JP); Tsutomu Honma, Fuchu (JP); Tetsuya Yano, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/340,728

(22) Filed: Jan. 27, 2006

(65) Prior Publication Data

US 2006/0172394 A1   Aug. 3, 2006

(30) Foreign Application Priority Data

Jan. 31, 2005 (JP) .............................. 2005-023977

(51) Int. Cl.
| | | |
|---|---|---|
| C12N 1/24 | (2006.01) | |
| C12N 1/21 | (2006.01) | |
| C12P 17/00 | (2006.01) | |
| C12P 11/00 | (2006.01) | |

(52) U.S. Cl. .................. 435/253.3; 435/117; 435/130; 435/252.34; 435/135

(58) Field of Classification Search ............. 435/252.1
See application file for complete search history.

(56) References Cited

U.S. PATENT DOCUMENTS

| | | | |
|---|---|---|---|
| 5,658,795 A | 8/1997 | Kato et al. ................ 435/262.5 |
| 5,665,597 A | 9/1997 | Imamura et al. .......... 435/253.3 |
| 5,670,315 A | 9/1997 | Yamamoto et al. ............. 435/6 |
| 5,679,568 A | 10/1997 | Imamura et al. .......... 435/262.5 |
| 5,753,466 A | 5/1998 | Yano et al. ................. 435/91.1 |
| 5,803,664 A | 9/1998 | Kawabata et al. ........... 405/128 |
| 5,807,736 A | 9/1998 | Kozaki et al. ............. 435/262.5 |
| 5,854,059 A | 12/1998 | Kozaki et al. ............... 435/262 |
| 5,863,789 A | 1/1999 | Komatsu et al. ............ 435/262 |
| 5,945,331 A | 8/1999 | Kozaki et al. ............... 435/262 |
| 5,962,305 A | 10/1999 | Mihara et al. ........... 435/262.5 |
| 5,993,658 A | 11/1999 | Kato et al. .................. 210/611 |
| 6,004,772 A | 12/1999 | Imamura et al. ............... 435/34 |
| 6,017,746 A | 1/2000 | Imamura et al. .......... 435/252.1 |
| 6,096,530 A | 8/2000 | Kato et al. ................ 435/253.3 |
| 6,472,191 B1 | 10/2002 | Yano et al. .................. 435/189 |
| 6,479,621 B2 | 11/2002 | Honma et al. ............... 528/361 |
| 6,586,562 B2 | 7/2003 | Honma et al. ............... 528/361 |
| 6,649,381 B1 | 11/2003 | Honma et al. ............... 435/135 |
| 6,660,516 B1 | 12/2003 | Imamura et al. ......... 435/252.8 |
| 6,686,439 B2 | 2/2004 | Kenmoku et al. ........... 528/272 |
| 6,803,444 B2 | 10/2004 | Suzuki et al. ............... 528/361 |
| 6,808,854 B2 | 10/2004 | Imamura et al. ............. 430/110 |
| 6,828,074 B2 | 12/2004 | Yano et al. ............... 430/109.1 |
| 6,853,477 B2 | 2/2005 | Nomoto et al. ............. 359/296 |
| 6,855,472 B2 | 2/2005 | Imamura et al. ......... 430/109.4 |
| 6,858,367 B2 | 2/2005 | Yano et al. .................. 430/109 |
| 6,858,417 B2 | 2/2005 | Yano et al. .................. 435/189 |
| 6,861,496 B2 | 3/2005 | Kenmoku et al. ........... 528/272 |
| 6,861,550 B2 | 3/2005 | Honma et al. ................ 560/53 |
| 6,864,074 B2 | 3/2005 | Yano et al. .................. 435/189 |
| 6,867,023 B2 | 3/2005 | Honma et al. ............... 435/135 |
| 6,869,782 B2 | 3/2005 | Kenmoku et al. .......... 435/130 |
| 6,908,720 B2 | 6/2005 | Kenmoku et al. ............ 430/97 |
| 6,916,861 B2 | 7/2005 | Nomoto et al. ............. 523/160 |
| 6,951,745 B2 | 10/2005 | Nomoto et al. ............. 435/118 |
| 7,056,708 B2 | 6/2006 | Kenmoku et al. .......... 435/130 |
| 7,153,622 B2 | 12/2006 | Honma et al. ............... 430/105 |
| 7,169,598 B2 | 1/2007 | Honma et al. ........... 435/253.3 |
| 2003/0032151 A1* | 2/2003 | Honma et al. ............... 435/135 |
| 2003/0194443 A1 | 10/2003 | Yano et al. .................. 424/497 |
| 2004/0005638 A1 | 1/2004 | Honma et al. ................ 435/7.1 |
| 2005/0208635 A1 | 9/2005 | Nomoto et al. ............. 435/135 |
| 2005/0250191 A1* | 11/2005 | Imamura et al. ............. 435/135 |
| 2006/0172398 A1 | 8/2006 | Nomoto et al. ............. 435/135 |
| 2006/0172399 A1 | 8/2006 | Nomoto et al. ............. 435/135 |
| 2006/0172400 A1 | 8/2006 | Nomoto et al. ............. 435/135 |
| 2006/0211100 A1* | 9/2006 | Kenmoku et al. .......... 435/135 |
| 2007/0054315 A1 | 3/2007 | Imamura et al. ............. 435/7.1 |

FOREIGN PATENT DOCUMENTS

| | | |
|---|---|---|
| JP | 2002-80571 | 3/2002 |
| JP | 2003-310292 | 11/2003 |

OTHER PUBLICATIONS

Biodegradable Plastics Research Group, ed., Biodegradable Plastics Handbook, NTS Inc., 1995, pp. 178 to 197.

* cited by examiner

*Primary Examiner*—Rebecca E. Prouty
*Assistant Examiner*—Md Younus Meah
(74) *Attorney, Agent, or Firm*—Fitzpatrick, Cella, Harper & Scinto

(57) ABSTRACT

Microorganisms showing higher productivity of unusual-polyhydroxyalkanoate (PHA) than ever by using an inexpensive substrate or under specific conditions are obtained from wild strains and mutant strains. The microorganisms are cultured with such substrates to synthesize an unusual-polyhydroxyalkanoate. The unusual-polyhydroxyalkanoate can be produced with high efficiency at low cost.

1 Claim, No Drawings

POLYHYDROXYALKANOATE SYNTHESIZING MICROORGANISM AND PROCESS OF PRODUCING POLYHYDROXYALKANOATE USING THE SAME

BACKGROUND OF THE INVENTION

1. Field of the Invention

The present invention relates to a polyhydroxyalkanoate synthesizing microorganism and a process of producing polyhydroxyalkanoate using the same.

2. Related Background Art

It has heretofore been reported that many microorganisms produce poly-3-hydroxy-n-butyric acid (hereinafter, sometimes referred to as "PHB" for short) and accumulate it in the bacterial cells (cf., Biodegradable Plastics Research Group, ed, "Biodegradable Plastics Handbook", NTS INC., p 178-197 (1995)). The polymers, like conventional plastics, can be used for the production of various products by melt processing or the like. Further, because of their biodegradability, they are advantageous in that they can be completely degraded by microorganisms in nature. Unlike most conventional synthetic high polymer compounds, few of them remain in the natural environment to cause environmental pollution.

PHB is a kind of "usual-PHA", that is, PHA composed of a monomer unit having an alkyl group in the side chain. On the other hand, taking into consideration wide application of PHA, for example, application as a functional polymer, "unusual-PHA", which is PHA that has introduced in the side chain a substituent other than alkyl groups is expected to be very useful. Examples of the substituent include those substituents that contain an aromatic ring and unsaturated hydrocarbons. PHAs can be produced by culturing microorganisms while feeding as substrates them with substituted alkanoates or substituted alkanes having substituents to be introduced.

For example, Japanese Patent Application Laid-Open No. 2002-80571 discloses the production of unusual-PHAs by various microorganisms including *Pseudomonas cichorii* YN2 strain, *Pseudomonas cichorii* H45 strain, *Pseudomonas jessenii* P161 strain, *Pseudomonas putida* P91-strain using as the substrates substituted alkanoates having a phenyl group, a phenoxy group or a cyclohexyl group in the side chain. Further, Japanese Patent Application Laid-Open No. 2003-310292 discloses the production of unusual-PHAs by *Pseudomonas cichorii* YN2 strain using as substrates various substituted alkanes having an aromatic ring in the side chain.

While as stated above, functionally useful unusual-PHAs are produced by some microorganisms, it is essential to decrease production cost of PHAs than ever in order to apply the unusual-PHAs to a wide variety of products as high polymer materials. For this purpose, one issue is to increase production efficiency of unusual-PHAs by microorganisms and another is to use less expensive substrates than ever in the production of unusual-PHAs. In particular, the substrates necessary for the production of PHAs in many cases are chemically synthesized and their production cost of PHAs largely depends on the price of the substrates. The substituted alkanoates, which are generally used as substrates, contain a carboxylic group having activity, so the production of PHAs with substituted alkanoates in most cases requires cumbersome operations such as protection and deprotection of carboxylic groups. This means an increase in the number of process steps and hence a higher price. On the other hand, when substituted alkanes are used as substrates, the number of process steps is smaller than that in the case of using the substituted alkanoates as substrates, so the price is relatively low. However, in most cases, the productivity of PHAs by the microorganisms is lower and the culturing method is more complicated than the case in which the substituted alkanoates are used as substrates. From the foregoing, it is desired that higher-productivity than ever be obtained by using substituted alkanes as substrates to produce PHAs at low cost.

Further, there has been a problem in that in the case of microorganisms with a high unusual-PHA productivity, for example, YN2 strain, the PHA productivity depends largely on the pH of the medium, that is, the PHA productivity decreases largely at pH values other than the optimum pH around pH7. In particular when the concentration of the substrate or medium is increased with a view to increase the productivity, pH tends to fluctuate beyond the buffering capability of the medium as culture proceeds, so the PHA productivity is unstable. Accordingly, it has been desired to produce stably PHAs against pH fluctuation.

SUMMARY OF THE INVENTION

It is an object of the present invention to provide a novel microorganism that can produce PHAs useful as biodegradable materials, functional materials and so on at high efficiency and at low cost and a process of producing PHAs using such microorganisms.

The inventors of the present invention have made extensive studies with a view to attaining the above-mentioned object, and as a result they have obtained microorganisms that produce PHAs at higher PHA productivity than conventional ones, and microorganisms that can efficiently produce PHAs from monomers that are less expensive than conventional ones from wild strains and mutant strains. In addition, they have obtained microorganisms that can produce PHAs efficiently in media that are at lower or higher pH than conventional ones from wild strains. Moreover, they have found that when alkanes are used as substrates, addition of dispersants to a medium results in a further increase in the PHA productivity by the microorganisms.

That is, an unusual-PHA producing bacterium according to the present invention includes *Pseudomonas* sp. AG32 strain (FERM BP-8586), *Pseudomonas* sp. KF767 strain (FERM BP-8589), *Pseudomonas* sp. TM90 strain (FERM BP-8587), *Pseudomonas* sp. TM109 strain (FERM BP-8588), and *Pseudomonas* sp. YN21M strain (FERM BP-8585) each capable of synthesizing a polyhydroxyalkanoate containing in a polymer molecule thereof at least one unit selected from the group consisting of units represented by formulae (1) to (4) shown below.

Further, the process of producing a polyhydroxyalkanoate according to the present invention relates to a process of producing a polyhydroxyalkanoate including a step of allowing a microorganism to synthesize a polyhydroxyalkanoate, wherein the microorganism is one strain selected from the group consisting of *Pseudomonas* sp. AG32 strain (FERM BP-8586), *Pseudomonas* sp. KF767 strain (FERM BP-8589), *Pseudomonas* sp. TM90 strain (FERM BP-8587), *Pseudomonas* sp. TM109 strain (FERM BP-8588), and *Pseudomonas* sp. YN21M strain (FERM BP-8585), and polyhydroxalkanoate to be synthesized is one having at least one unit selected from the group consisting of units (1) to (4) described hereinafter in the polymer molecule.

According to the present invention, a novel microorganism is provided and polyhydroxyalkanoates useful as biodegradable materials and functional materials can be produced at high efficiency and at low cost using the microorganism.

DESCRIPTION OF THE PREFERRED EMBODIMENTS

The microorganism having a PHA synthesizing ability according to the present invention can be clearly distinguished from conventional PHA producing microorganisms in high productivity of polyhydrokyalkanoate (unusual-PHA) containing in polymer molecules at least one unit selected from the group consisting of the following units (1) to (4).

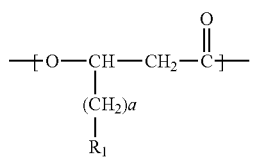

(1)

$a = 1\text{-}8$ wherein a is an integer selected from the range shown in the formula; $R_1$ represents at least one residue represented by any one of formulae (5) to (12); provided that when a plurality of units represented by formula (1) are present, each unit independently has the meaning defined above;

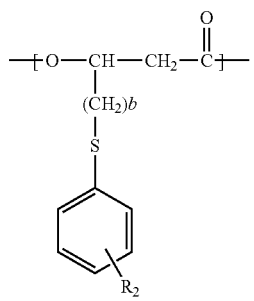

(2)

$b = 1\text{-}7$ wherein $R_2$ represents a substituent to the aromatic ring and represents a hydrogen atom, a halogen atom, a CN group, an $NO_2$ group, COOR' where R' represents any one of H, Na, K, $CH_3$ and $C_2H_5$, $SO_2R''$ where R'' represents any one of OH, ONa, OK, a halogen atom, $OCH_3$ and $OC_2H_5$, a $CH_3$ group, a $C_2H_5$ group, a $C_3H_7$ group, a $(CH_3)_2$—CH group or a $(CH_3)_3$—C group; b is an integer selected from the range shown in the formula, provided that when a plurality of units represented by formula (2) are present, each unit independently has the meaning defined above;

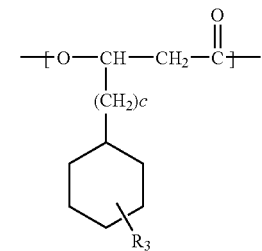

(3)

$c = 0\text{-}8$ wherein $R_3$ represents a substituent to the cyclohexyl group and represents a hydrogen atom, a CN group, an $NO_2$ group, a halogen atom, a $CH_3$ group, a $C_2H_5$ group, a $C_3H_7$ group, a $CF_3$ group, a $C_2F_5$ group or a $C_3F_7$ group; c is an integer selected from the range shown in the formula, provided that when a plurality of units represented by formula (3) are present, each unit independently has the meaning defined above;

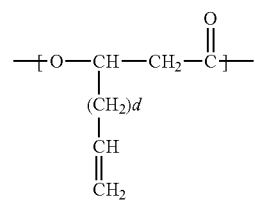

(4)

$d = 1\text{-}8$ wherein d is an integer selected from the range shown in the formula, provided that when a plurality of units represented by formula (4) are present, each unit independently has the meaning defined above;

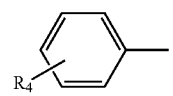

(5)

wherein $R_4$ represents a substituent to the aromatic ring; $R_4$ represents a hydrogen atom, a halogen atom, a CN group, an $NO_2$ group, a $CH_3$ group, a $C_2F_5$ group, a $C_3H_7$ group, a CH=$CH_2$ group, a $CF_3$ group, a $C_2H_5$ group, or a $C_3F_7$ group, provided that when a plurality of units are present, each unit independently has the meaning defined above;

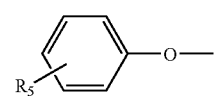

(6)

wherein $R_5$ represents a substituent to the aromatic ring; $R_5$ represents a hydrogen atom, a halogen atom, a CN group, an $NO_2$ group, a $CH_3$ group, a $C_2H_5$ group, a $C_3H_7$ group, an $SCH_3$ group, a $CF_3$ group, a $C_2F_5$ group, or a $C_3F_7$ group, provided that when a plurality of units are present, each unit independently has the meaning defined above;

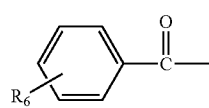

(7)

wherein $R_6$ represents a substituent to the aromatic ring; $R_6$ represents a hydrogen atom, a halogen atom, a CN group, an $NO_2$ group, a $CH_3$ group, a $C_3H_7$ group, a $CF_3$ group, a $C_2F_5$ group, or a $C_3F_7$ group, provided that when a plurality of units are present, each unit independently has the meaning defined above;

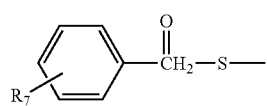

(8)

wherein $R_7$ represents a substituent to the aromatic ring and represents a hydrogen atom, a halogen atom, a CN group, an $NO_2$ group, COOR' where R' represents any one of H, Na, K, $CH_3$ and $C_2H_5$, $SO_2R''$ where R" represents any one of OH, ONa, OK, a halogen atom, $OCH_3$ and $OC_2H_5$), a $CH_3$ group, a $C_2H_5$ group, a $C_3H_7$ group, a $(CH_3)_2$—CH group or a $(CH_3)_3$—C group, provided that when a plurality of units are present, each unit independently has the meaning defined above;

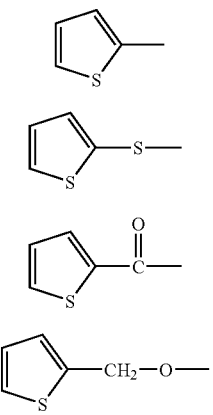

(9)

(10)

(11)

(12)

Hereinafter, the present invention and related matter will be explained in more detail by referring to items.

<PHA>

The "unusual-PHAs" produced according to the present invention have a basic skeleton as a biodegradable resin and therefore, while they can be used like conventional plastics in the production of various products by melting and other processes, they have peculiar properties, unlike synthetic high polymers derived from petroleum, that they can be degraded by organisms and incorporated into the circulation of substances in nature. Therefore, they need not be burned when disposed and thus are useful materials also from the viewpoint of preventing environmental pollution and global warming. They can be used as plastics with which environment conservation can be achieved. Further, by utilizing the function and physical properties ascribable to various functional groups in the unusual-PHAs, they can be expected to be used as various functional materials, for example, medical flexible members.

As an example of the unusual-PHAs produced by the process of the present invention, PHAs that contain at least one unit selected from the group consisting of units (1) to (4) described above can be mentioned of. The above-mentioned PHAs are generally isotactic polymers composed of R-forms only.

<PHA-Producing Microorganisms>

Strains YN21M, AG32, KF767, TM90, and TM109, which are the novel microorganisms of the present invention, use alkanoates or alkanes as substrates to produce PHAs containing novel monomer units derived from alkanoates or alkanes of the present invention and accumulate them in the bacterial cells. They exhibit higher productivity than the conventionally known unusual-PHA-producing microorganisms with respect to specified substrates or at specified pH of the medium. The novel microorganisms have been found in the environment or from among mutants of known PHA-producing microorganisms by screening by the inventors of the present invention. Hereinafter, details of the strains YN21M, AG32, KF767, TM90, and TM109 are shown. It is noted that either of these strains or YN21 strain which is a parent strain of the YN21M strain has been deposited at International Patent Organism Depositary, National Institute of Advanced Industrial Science and Technology at Tsukauba Central 6, 1-1, Hiagashi 1-Chome, Tsukuba-shi, Ibaraki-ken, Japan. The accession numbers for the respective strains are as follows:

Pseudomonas sp. AG32 strain: FERM BP-8586,
Pseudomonas sp. KF767 strain: FERM BP-8589,
Pseudomonas sp. TM90 strain: FERM BP-8587,
Pseudomonas sp. TM109 strain: FERM BP-8588,
Pseudomonas sp. YN21M strain: FERM BP-8585

<Mycological Properties of YN21M Strain>

This strain was obtained by a mutagenic treatment of a Pseudomonas sp. YN21 strain. Mycological properties of the strain are described below.

1) Morphological Properties
Shape and size of the cell: bacillus, 0.8 μm×1.5 to 2.0 μm
Polymorphism of the cell: none
Mobility: present
Spore formation: none.
Gram's stain: –
Colony form: circular, entire margin is smooth, low convexity, smooth surface layer, lustrous, translucent 2) Physiological Properties
Catalase activity: +
Oxidase activity: +
O/F test: oxidized form
Nitrate reduction: +
Indole production: –
Arginine dihydrolase: +
Esculin hydrolysis: –
Gelatin-hydrolysis: –
Fluorochrome production on King's B agar: +
Accumulation of poly-β-hydroxybutyric acid: –

Tween 80 hydrolysis: +
Growth at the temperature of 41° C.: −
Gluconic acid reduction: −
Levan production: −
Potato rot: −
Tobacco-hypersensitive response: −
Sucrose: −
Casein: −
Tyrosinase: +
Hydrogen sulfide: −
Pectin: −
Lecithinase: −
Litmus milk: B
Starch: −

3) Substrate Assimilabilities
Glucose: +
Sucrose: −
L-arabinose: +
D-arabinose: −
D-mannose: +
D-mannitol: −
Maltose: −
Gluconic acid: +
D-xylose: (+)
Raffinose: −
Salicin: −
Glycerin: +
D-cellobiose: −
D-melezitose: −
Lactose: −
Galactose: +
D-sorbitol: −
α-methyl-D-glucoside: −
D-ribose: (+)
Sucrose: −
Inositol: −
D-fructose: +
L-rhamnose: −
Dulcitol: −
Melibiose: −
Adonitol: −
Starch: −
Erythritol: −
Trehalose: −
Betaine: +
DL-lactic acid: −
D-tartaric acid: −
L-tartaric acid: (+)
Mesotartaric acid: +
n-Capric acid: +
L-malic acid: (+)
Citric acid: +
D-saccharate: +
Levulinic acid: +
Mesaconic acid: −
Malonic acid: +
Succinic acid: +
Acetic acid: +
Propionic acid: +
n-Butyric acid: +
Formic acid: −
Glutaric acid: +
D-quinic acid: +
Sebacic acid: +
p-Hydroxybenzoic acid: +
Anthranilic acid: −
Pelargonic acid: +
Glyceric acid: +
γ-aminobutyric acid: +
L-leucine: +
L-serine: +
Histidine: +
L-isoleucine: +
L-arginine: +
β-alanin: +
L-tyrosine: +
L-valine: +
Homoserine: −
Sarcosine: +
Triacetin: +
Trigonelline: +
5-Phenylvaleric acid: +
3-Hydroxybutyric acid: +
L-asparagine: +

<Mycological Properties of AG32 Strain>

This strain was newly obtained from the environment. Mycological properties of the strain of the present invention are described below.

1) Morphological Properties
Shape of the cell: *bacillus*
Gram's stain: −

2) Physiological Properties
Oxidase activity: +
Q/F test: oxidized form
Nitrate reduction: −
Indole production: −
Arginine dihydrolase: +
Gelatin hydrolysis: +
Fluorochrome production on King's B agar: +
Tween 80 hydrolysis: +
Growth at the temperature of 40 C.°: −
Gluconic acid reduction: +
Levan production: −
Potato rot: −
Tobacco-hypersensitive response: −
Lecithinase: +
Casein: +
Catalase: +
PHB accumulation: −

3) Substrate-Assimilation Abilities
Glucose: +
Sucrose: −
D-mannitol: +
Maltose: −
Lactose: −
Galactose: +
D-sorbitol: −
Inositol: +
L-rhamnose: −
Adonitol: −
Erythritol: −
Trehalose: −
DL-lactic acid: +
D-tartaric acid: −
L-tartaric acid: +
Mesotartaric acid: +
D-saccharate: +
Mesaconic acid: −
Propionic acid: +
n-Butyric acid: +
Ethanol: −

Propylene glycol: −

<Mycological Properties of KF767 Strain>

This strain was newly obtained from the environment. Mycological properties of the strain of the present invention are described below.

1) Morphological Properties
Shape of the cell: *bacillus*
Gram's stain: −

2) Physiological Properties
Oxidase activity: +
O/F test: oxidized form
Indole production: −
Arginine dihydrolase: +
Fluorochrome production on King's B agar: +
Growth at the temperature of 40 C.°: −
Catalase: +
PHB accumulation: −

3) Substrate-Assimilation Abilities
Glucose: +
Sucrose: −
Maltose: −
Lactose: −
D-sorbitol: −
Adonitol: −
Erythritol: −
Trehalose: −
DL-lactic acid: +
D-saccharate: +
Mesaconic acid: −
Propionic acid: +
n-Butyric acid: +

4) Partial Base Sequence a) 16S rDNA (SEQ ID NO: 1)
```
CTGGCGGCAGGCCTAACACATGCAAGTCGAGCGGATGAAGAGAGCTTGCT
CTCTGATTCAGCGGCGGACGGGTGAGTAATGCCTAGGAATCTGCCTGGTA
GTGGGGGACAACGTTTCGAAAGGAACGCTAATACCGCATACGTCCTACGG
GAGAAAGCAGGGGACCTTCGGGCCTTGCGCTATCAGATGAGCCTAGGTCG
GATTAGCTAGTTGGTGAGGTAATGGCTCACCAAGGCGACGATCCGTAACT
GGTCTGAGAGGATGATCAGTCACACTGGAACTGAGACACGGTCCAGACTC
CTACGGGAGGCAGCAGTGGGGAATATTGGACAATGGGCGAAACCCTGATC
CAGCCATGCCGCGTGTGTGAAGAAGGTCTTCGGATTGTAAAGCACTTTAA
GTTGGGAGGAAGGGCAGTAGATTAATACTCTGCTGTTTTGAGGTTACCGA
CAGAATAAGCACCGGCTAACTCTGTGCCAGCAGCCGCGGTAATACAGAGG
GTGCAAGCGTTAATCGGAATTACTGGGCGTAAAGCGCGCGTAGGTGGTTT
GTTAAGTTGGATGTGAAAGCCCCGGGCTCAACCTGGGAACTGCATTCAAA
ACTGACAAGCTAGAGTATGGTAGAGGGTGGTGGAATTTCCTGTGTAGCGG
TGAAATGCGTAGATATAGGAAGGAACACCAGTGGCGAAGGCGACCACCTG
GACTGATACTGACACTGAGGTGCGAAAGCGTGGGGAGCAAACAGGATTAG
ATACCCTGGTAGTCCACGCCGTAAACGATGTCAACTAGCCGTTGGGAGCC
TTGAGCTCTTAGTGGCGCAGCTAACGCATTAAGTTGACCGCCTGGGGAGT
ACGGCCGGAAGGTTAAAACTCAAATGAATTGACGGGGCCCGCACAAGCG
GTGGAGCATGTGGTTTAATTCGAAGCAACGCGAAGAACCTTACCAGGCCT
TGACATCCAATGAACTTTCCAGAGATGGATTGGTGCCTTCGGGAACATTG
AGACAGGTGCTGCATGGCTGTCGTCAGCTCGTGTCGTGAGATGTTGGGTT
AAGTCCCGTAACGAGCGCAACCCTTGTCCTTAGTTACCAGCACGTAATGG
TGGGCACTCTAAGGAGACTGCCGGTGACAAACCGGAGGAAGGTGGGGATG
ACGTCAAGTCATCATGGCCCTTACGGCCTGGGCTACACACGTGCTACAAT
GGTCGGTACAGAGGGTTGCCAAGCCGCGAGGTGGAGCTAATCCCATAAAA
CCGATCGTAGTCCGGATCGCAGTCTGCAACTCGACTGCGTGAAGTCGGAA
TCGCTAGTAATCGCGAATCAGAATGTCGCGGTGAATACGTTCCCGGGCCT
TGTACACACCGCCCGTCACACCATGGGAGTGGGTTGCACCAGAAGTAGCT
AGTCTAACCTTCGGGGGACGGTTACCACGGTGTGATTCATGACTGGGGG
AAGTCGAACAA
``` b) gyrB (SEQ ID NO: 2)
```
TCCTACAAGGTATCCGGCGGCCTGCACGGCGTAGGTGTGTCGGTAGTGAA
CGCCCTGTCTGAAGAGCTAGTCCTCACCGTTCGCCGTAGCGGCAAGATCT
GGGAACAGACCTACGTCCATGGTGTTCCGCAGGAGCCGATGAAGATCGTT
GGCGACAGCGAAACCACTGGCACCCAGATCCACTTCAAGGCTTCCAGCGA
AACCTTCAAGAACATCCACTTCAGCTGGGACATCCTGGCCAAGCGGATTC
GTGAACTGTCCTTCCTCAACTCCGGTGTCGGTATCGTCCTCAAGGACGAG
CGCAGCGGCAAGGAAGAGCTGTTCAAGTACGAACGCGGCCTGCGTGCGTT
CGTTGAATACCTGAACACCAACAAGACCCCGGTCAACCAGGTGTTGCACT
TCAACATCCAGCGTGAAGACGGCATTGGCGTGGAAATCGCCCTGCAGTGG
AACGACAGCTTCAACGAGAACCTGTTGTGCTTCACCAACAACATTCCGCA
GCGCGATGGCGGTACTCACCTGGTGGGTTTCCGTTCCGCACTGACGCGTA
ACCTGAACACCTATATCGAAGCTGAAGGCCTGGCGAAGAAGCACAAGGTC
GCCACCACCGGTGACGACGCCCGTGAAGGCCTGACCGCGATCATTTCGGT
AAAAGTGCCGGATCCGAAGTTCAGCTCCCAGACCAAGGACAAGCTGGTCT
CTTCCGAAGTGAAGACCCGGTCGAACAGGAAATGGGCAAGTACTTCTCC
GACTTCCTGCTGGAAAACCCGAACGAAGCCAAGCTGGTTGTCGGCAAGAT
GATCGACGCGGCACGTGCTCGTGAAGCCGCGCGCAAGGCCCGTGAGATGA
CCCGCCGTAAAGGCGCACTGGACATCGCTGGCCTGCCGGGCAAACTGGCT
GAT
``` c) rpoD (SEQ ID NO: 3)
```
GAGCTCCTCACGCGTGAAGGCGAAATCGAAATCGCCAAGCGTATTGAAGA
GGGCATCCGTGAAGTGATGAGCGCAATCGCGCACTTCCCTGGCACGGTTG
ATCATATTCTCTCCGAATACACTCGCGTCACCACCGAAGGTGGCCGCCTG
TCCGACGTCCTGAGCGGTTATATCGACCCGGACGACGGTATTGCGCCGCC
TGCAGCGGAGGTGCCACCGCCGATCGACACCAAGACCGCGAAAGCGGATG
ACGATTCCGACGACGATGACGCCGAAGCTTCCGATGACGAAGAAGAAGCC
GAAAGCGGTCCGGATCCGATCATCGCCGCCCAGCGCTTTGGTGCTGTCGC
CGATCAGATGGAAATCACCCGCAAGGCGCTGAAAAAGCACGGTCGCCACA
ACAAGCTGGCGATTGCCGAGCTGTTGGCCCTTGCCGACCTGTTCATGCCG
ATCAAACTGGTTCCGAAGCAATTCGAAGGCCTGGTCGAGCGTGTGCGCAG
CGCCCTGGATCGTCTGCGTCAGCAAGAGCGTGCAATCATGCAGCTCTGCG
TTCGTGATGCACGCATGCCGCGTGCTGACTTCCTGCGCCAGTTCCCGGGC
AACGAAGTGGACGAAAGCTGGAGCGATGCACTGGCCAAAGGCAAAAGCAA
ATACGCTGAAGCCATCGGTCGCGTGCAGCCGGACATCATTCGCTGCCAGC
AGAAGCTGACCGCGCTGGAAACCGAAACCGGTTTGACGATCGCCGAGATC
AAGGACATCAACCGTCGCATGTCGATCGGTGAGGCCAAGGCCCGCCGCGC
G
```

<Mycological Properties of TM90 Strain>

This strain was newly obtained from the environment. Mycological properties of the strain of the present invention are described below.

1) Morphological Properties
Shape of the cell: *bacillus*
Gram's stain: −

2) Physiological Properties
Oxidase activity: +
O/F test: oxidized form
Nitrate reduction: −
Indole production: −
Arginine dihydrolase: +
Gelatin hydrolysis: −
Fluorochrome production on King's B agar: +
Tween 80 hydrolysis: +
Growth at the temperature of 40°0 C.: −
Gluconic acid reduction: −
Levan production: +−
Potato rot: −
Tobacco-hypersensitive response: −
Lecithinase: −
Casein: +
Catalase: +
PHB accumulation: −

3) Substrate-Assimilation Abilities
Glucose: +
Sucrose: −
D-mannitol: −
Maltose: −
Lactose: −
Galactose: +
D-sorbitol: +
Inositol: −
L-rhamnose: −

Adonitol: −
Erythritol: −
Trehalose: −
DL-lactic acid: +
D-tartaric acid: −
L-tartaric acid: −
Mesotartaric acid: −
D-saccharate: +
Mesaconic acid: −
Propionic acid: +
n-Butyric acid: +
Ethanol: +
Plopylene glycol: +.

<Mycological Properties of TM109 Strain>

This strain was newly obtained from the environment. Mycological properties of the strain of the present invention are described below.

1) Morphological Properties
Shape of the cell: bacillus
Gram's stain: −

2) Physiological Properties
Oxidase activity: +
O/F test: oxidized form
Nitrate reduction: −
Indole production: −
Arginine dihydrolase: +
Gelatin hydrolysis: −
Fluorochrome production on-King's B agar: +W
Tween 80 hydrolysis: −
Growth at the temperature of 40 C.°: −
Gluconic acid reduction: −
Levan production: −
Potato rot: −
Tobacco-hypersensitive response: −
Lecithinase: −
Casein: −
Catalase: +
PHB accumulation: −

3) Substrate-Assimilation Abilities.
Glucose: +
Sucrose: −
D-mannitol: +
Maltose: −
Lactose: −
Galactose: +
D-sorbitol: −
Inositol: −
L-rhamnose: −
Adonitol: −
Erythritol: −
Trehalose: −
DL-lactic acid: +
D-tartaric acid: +
L-tartaric acid: −
Mesotartaric acid: −
D-saccharate: +
Mesaconic acid: −
Propionic acid: +
n-Butyric acid: +
Ethanol: +
Plopylene glycol: +

From the above-mentioned mycological properties, search has been made with reference to Bergey's Manual of Systematic Bacteriology, Volume 1, 1984, and Bergey's Manual of Determinative Bacteriology, 9th Ed. (1994) and as well as homology search based on a partial base sequence for the KF767 strain.

The results indicate that all the strains in question belong to *Pseudomonas* sp. Therefore, the strains were named *Pseudomonas* sp. YN21M, *Pseudomonas* sp. AG32, *Pseudomonas* sp KF767, *Pseudomonas* sp. TM90, and *Pseudomonas* sp. TM109, respectively.

Note that the above-mentioned five novel microorganisms differ from the conventional strains in the following points.

YN21M and TM109 have a PHA productivity higher than that of the conventional strains under culture conditions around neutral pHs. KF767 has a PHA productivity higher than that of the conventional strains under acidic culture conditions. AG32 strains and TM90 strains each have a PHA productivity higher than that of the conventional strains under basic culture conditions. In addition to these properties, the YN21M strain can show the difference in physiological properties and substrate assimilability, such as nitrate reductivity, generation of indole, acidification of glucose, arginine hydrolase activity, D-mannitol assimilability, from those of the *Pseudomonas cichorii* YN2 (FERM BP-7375), a conventional strain. Similarly, the YN21M strain is different from *Pseudomonas cichorii* H45 (FERM BP-7374) in the properties of nitrate reductivity, arginine dihydrolase activity, L-arabinose assimilability, and D-mannitol assimilability, from *Pseudomonas jessenii* P161 (FERM BP-7376) in the property of D-mannitol assimilability, and from *Pseudomonas putida* P91 (FERM BP-7373) in the properties of nitrate reductivity, L-arabinose assimilability, and D-mannitol assimilability, respectively.

Further, the AG32 strain is different from the YN2 strain, which is a conventional strain, in the properties of indole productivity, arginine dihydrolase activity, and gelatin-hydrolytic activity, from the H45 strain in the properties of arginine dihydrolase activity and gelatin-hydrolytic activity, from the P161 strain in the property of gelatin-hydrolytic activity, and from the P91 strain in the property of D-mannitol assimilability, respectively. Further, the KF767 strain is different from the YN2 strain, which is a conventional strain, in the properties of indole productivity and arginine dihydrolase activity, from the H45 strain in the property of arginine dihydrolase activity, and from the P91 strain in the property of indole productivity, respectively. The TM90 strain is different from the YN2 strain, which is a conventional strain, in the properties of indole-productivity and arginine dihydrolase activity, from the H45 strain in the properties of arginine dihydrolase activity and D-mannitol assimilability, and from the P161 strain in the properties of nitrate reductivity and D-mannitol assimilability, respectively. The TM109 strain is different from the YN2 strain, which is a conventional strain, in the properties of indole productivity, arginine dihydrolase activity, and D-mannitol assimilability, from the P161 strain in the property of nitrate reductivity, and from the P91 strain in the property of D-mannitol assimilability, respectively.

<Substrate>

The PHAs that contain at least one unit selected from the group consisting of units represented by general formulae (1) to (4) can be produced by culturing the above-mentioned novel microorganisms of the present invention in a medium that contains an alkanoate or alkane serving as a substrate for introducing the unit represented by one of the general formulae (1) to (4) above. The alkanoate or alkane that serves as a substrate may be of any type as far as it is an alkanoate or alkane that can be converted into a corresponding monomer unit of the PHA by the action of a microorganism of the present invention and it has a substituent in the side chain depending on the chemical structure of the target PHA. For example, the alkanoates having chemical structures represented by general formulae (13) to (16) can be used preferably.

Here, the general formula (13) is shown as follows:

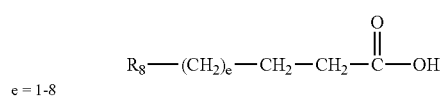

(13)

$e = 1-8$ wherein e is an integer selected from the range shown in the formula; $R_8$ includes a residue having a phenyl structure or an thienyl structure;

the general formula (14) is shown as follows:

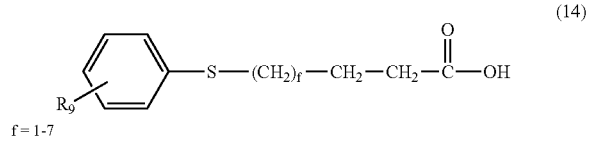

(14)

$f = 1-7$ wherein $R_9$ represents a substituent to the aromatic ring and represents a hydrogen atom, a halogen atom, a CN group, an $NO_2$ group, COOR', $SO_2R''$ (where R' represents any one of H, Na, K, $CH_3$, and $C_2H_5$, and R'' represents any one of OH, ONa, OK, a halogen atom, $OCH_3$, and $OC_2H_5$), a $CH_3$ group, a $C_2H_5$ group, a $C_3H_7$ group, a $(CH_3)_2$—CH group or a $(CH_3)_3$—C group; f is an integer selected from the range shown in the formula;

the general formula (15) is shown as follows:

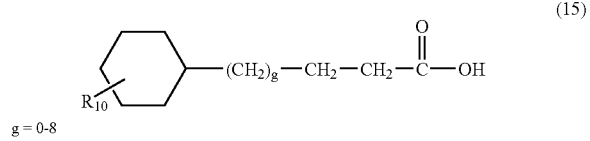

(15)

$g = 0-8$ wherein $R_{10}$ represents a substituent to the cyclohexyl ring and represents a hydrogen atom, a CN group, an $NO_2$ group, a halogen atom, a $CH_3$ group, a $C_2H_5$ group, a $C_3H_7$ group, a $CF_3$ group, a $C_2F_5$ group, or a $C_3F_7$; g is an integer selected from the range shown in the formula;

the general formula (16) is shown as follows:

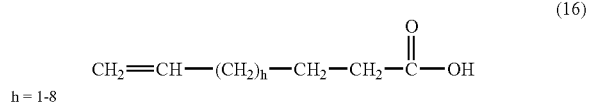

(16)

$h = 1-8$ wherein h is an integer selected from the range shown in the formula. Similarly, examples of the alkane that can be used in the present invention include those alkanes having chemical structures that, correspond to the general formulae (13) to (16) in which the alkanoates are replaced by corresponding alkanes.

The novel microorganisms YN21M and TM109 strains of the present invention can produce unusual-PHAs at high yields by utilizing the above-mentioned substrates. Specifically, when 5-phenylvaleric acid is used as a substrate, the YN21M strain can produce a PHA having a 3-hydroxy-5-phenylvalerate unit at a higher yield than that of the conventionally known microorganisms. In addition, when 5-phenylvaleric acid is used as a substrate, the TM 109 strain can produce a PHA having a 3-hydroxy-5-phenylvalerate unit at a higher yield than that of the conventionally known microorganisms. Since generally alkanes can be chemically synthesized at lower costs than alkanoates, use of alkanes leads to a reduction in the production cost for unusual-PHAs. The YN21M strain, which is one of the novel microorganisms of the present invention can use alkanes to produce unusual-PHAs at higher yields than conventional cases. Specifically, when n-amylbenzene is used, the YN21M strain can produce a PHA having a 3-hydroxy-5-phenylvalerate unit in a higher yield than that of the conventional known microorganisms. It is desirable that the content ratios of the above-mentioned substrates be selected to be within the range of 0.01% to 1% (w/v) per medium.

<Culture>

The culturing methods which can be used in the present invention include a liquid culture method and in addition, a batch culture method, a fed batch culture method, a semi-continuous culture method, a continuous culture method and combinations of these and are not particularly limited. The forms of the liquid batch culture method include, for example, a method in which a flask is used, and a method in which a jar fermenter is used. The media that can be used in the methods of the present invention may be any media that contain components with which microorganisms can grow, such as a phosphorus source (for example, phosphates) and a nitrogen source (for example, ammonium salts, and nitrates) at an appropriate concentration.

Further, to promote good cell growth and increase the productivity of PHAs accompanying it, suitable amounts of essential trace elements can be added to the above-mentioned media. For example, it is very effective to add trace components solution shown below to the medium in amounts of about 0.3% (v/v). The addition of such a solution of trace components is to supply trace metal elements and so on used upon the growth of microorganisms.

(Composition of Trace Components Solution)

Nitrilotriacetate: 1.5; $MgSO_4$: 3.0; $MnSO_4$: 0.5; NaCl: 1.0; $FeSO_4$: 0.1; $CaCl_2$: 0.1; $CoCl_2$: 0.1; $ZnSO_4$: 0.1; $CuSO_4$: 0.1; $AlK(SO_4)_2$: 0.1; $H_3BO_3$: 0.1; $Na_2MoO_4$: 0.1; $NiCl_2$: 0.1 (g/L)

In addition, a nutrient such as yeast extract, polypeptone, meat extract, or corn steep liquor can be further added to the medium as a substrate which facilitates the proliferation of the microorganism.

Furthermore, an energy source or carbon source which is consumed by the growth of microorganisms can be further added to the medium. Examples of the energy source or the carbon source which can be added include aldoses such as glyceroaldehyde, erythrose, arabinose, xylose, glucose, galactose, mannose, and fructose, alditols such as glycerol, erythritol, and xylitol, aldonic acids such as gluconic acid, uronic acids such as glucuronic acid and galacturonic acid, and disaccharides such as maltose, sucrose, and lactose.

In place of the above-mentioned sugars, organic acids or salts thereof, more specifically organic acids that participate in the TCA cycle and organic acids that can be derived from the TCA cycle through a few steps, such as one or two steps, of biochemical reactions or water-soluble salts thereof can be used. Examples of the organic acid or salts thereof that can be used include hydroxycarboxylic acids or oxocarboxylic acids, such as pyruvic acid, oxaloacetic acid, citric acid, isocitric acid, ketoglutaric acid, succinic acid, fumaric acid, malic acid, lactic acid, and water-soluble salts thereof. Alternatively, amino acids or salts thereof, for example, aspartic acid, glutamic acid or salts thereof can be used. When the organic acids or salts thereof are added to the medium, it is preferable to select one or more compounds from the group consisting of pyruvic acid, oxaloacetic acid, citric acid, isocitric acid, ketoglutaric acid, succinic acid, fumaric acid, malic acid, lactic acid and salts thereof, add the selected compound(s) to the medium, and have it (or them) dissolved therein. Alternatively, when amino acids or salts thereof are added to the medium, it is preferable to select one or more compounds from the group consisting of aspartic acid, glutamic acid and salts thereof, add the selected compound(s) to the medium and have it (or them) dissolved therein.

The concentrations of the carbon source for the growth of microorganisms and of the above-mentioned co-existing substrates to be added in the medium as an energy supply source for the production of PHAs may be selected within the range of, usually 0.05% to 5% (w/v), preferably 0.2% to 2% (w/v), per medium.

When alkanes are used as substrates for synthesizing PHAs, dispersants having a surfactant activity can be added to the medium in appropriate concentrations to increase the productivity of PHAs. The reason for this may be that the dispersant improves the solubility of alkanes in the medium, suppresses volatility of the alkanes and decreases inhibitory actions against the growth of microorganisms and PHA production. Even in the case of the YN21M strain that can produce PHAs at high yields using alkanes, addition of dispersants enables the productivity of PHAs to be increased. Any surfactants that do not inhibit the growth and activity of microorganisms considerably and do not remain in the PHAs recovered from the microorganism cells can be used as the dispersants. For example, polyoxyethylene sorbitan fatty acid esters, polyoxyalkylene ethers, polyoxyalkylene glycols, polyethers and so on, which are nonionic surfactants, can be used. These include defoaming agents generally used in culturing microorganisms. Accordingly, such surfactants can be added to the medium doubling as deforming agents.

The concentration of the dispersant can be set appropriately depending on the kind of the dispersant and the purpose. For example, a concentration within the range of 0.1 to 1 ml/liter, more preferably a concentration of about 0.5 ml/liter can be suitably used.

The culture temperature may be any temperature at which microorganism strains to be used can grow well. Usually, the culture temperature is appropriately selected to be within the range of 15 to 37° C., preferably 20 to 30° C.

The culture pH may be any pH which has a good range for the growth of the microorganism to be used and for the production of the target PHAs. It is also preferable to control pH to be within such a range. The pH can be controlled by adopting methods generally used in culturing microorganisms, such as a method in which the medium is imparted with a buffering ability in advance and the buffering ability is controlled; and a method in which acid or alkali is added as appropriate according to a change in pH of the medium during culture to control the pH of the medium. When the concentration of substrate or medium is increased in order to increase the productivity of PHAs, pH may in some cases vary with time course of culture to above the buffering ability of the medium. Also, it is often difficult to control the pH of the medium by addition of acid or alkali from the viewpoints of requirements for equipment and convenience.

The KF767 strain, which is a novel microorganism of the present invention can produce unusual-PHAs relatively stably in high yields even when the pH of the medium during culture is shifted to some extent to the acidic side. Specifically, when 5-phenylvaleric acid is used as a substrate, the KF767 strain can produce PHAs with a 3-hydroxy-5-phenylvalerate unit in higher yields as compared with the conventional microorganisms in acidic media at pH 5.0 to 6.0.

The AG32 and TM90 strains, which are novel microorganism of the present invention can produce unusual-PHAs relatively stably in high yields even when the pH of the medium during culture is shifted to some extent to the basic side. Specifically, when 5-phenylvaleric acid is used as a substrate, the AG32 and TM90 strains can produce PHAs with a 3-hydroxy-5-phenylvalerate unit in higher yields as compared with the conventional microorganisms in basic media at pH 7.5 to 8.5.

The techniques to cause microorganisms to produce and accumulate PHAs therein include a single stage culture method including culturing a microorganism in a medium that contains a phosphate and a nitrogen source such as an ammonium salt or a nitrate in which a substrate is added in a predetermined concentration. In addition, a two-stage culture method including performing culture in two stages can be adopted. The two-stage culture includes a first culture in which the microorganism is once sufficiently cultured in a medium that contains a phosphate and a nitrogen source such as an ammonium salt or a nitrate in addition to a substrate in a predetermined concentration, and then a second culture in which while controlling the concentration of the nitrogen source such as ammonium chloride contained in a medium which contains the substrate in a predetermined concentration, the microorganism cells obtained in the first culture are transferred to the medium, and further cultured to cause the microorganism to produce and accumulate therein PHAs. When the two-stage culture method is adopted, the productivity of PHAs is sometimes increased.

Since the PHAs to be produced accumulate in the cells of the microorganisms, the PHAs can be separated from the medium easily by culturing a microorganism to grow and collecting the cells of the microorganism that produce and accumulate PHAs. The target PHAs can be recovered from the microorganism after washing and drying the collected cells.

The PHAs can be recovered from the microorganism cells by applying methods usually used. For example, the simplest method is extraction with an organic solvent such as chloroform, dichloromethane, or acetone. Besides the above-mentioned solvents, dioxane, tetrahydrofuran and acetonitrile may be used in some cases. Further, in a working environment where use of organic solvents is undesirable, a method can be adopted in which the microorganism cells are physically destructed by any one method selected from the group consisting of treatment with a surfactant such as SDS, treatment with an enzyme such as lysozyme, treatment with a chemical agent such as hypochlorite, ammonia or EDTA, an ultrasonic breaking method, a homogenizing method, a pressure rupturing method, a bead impact method, a milling method, a macerating method, and a freezing and thawing method, and then cell components other than the PHAs are removed to recover the PHAs.

The unusual-PHAs to be produced by the method of the present invention can contain a plurality of monomer units and can be designed appropriately taking into consideration the functionality and physical properties and the like of the polymer required. That is, by allowing a plurality of alkanoates or alkanes that are substrates for producing target PHAs to coexist in the medium, PHAs containing a plurality of monomer units can be produced.

EXAMPLES

Now, the present invention is explained in more detail by way of examples. However, while these examples are examples of best mode for carrying out the present invention, the present invention should not be considered to be limited to the examples.

Reference Example 1

*Pseudomonas* sp. AG32, *Pseudomonas* sp. KF767, *Pseudomonas* sp. TM90, and *Pseudomonas* sp. TM109, which are novel microorganisms of the present invention as well as *Pseudomonas* sp. YN21 (FERM BP-08569) as a parent strain of *Pseudomonas* sp. YN21M were obtained by the following methods. That is, M9 medium containing 0.5% of polypeptone, 0.1% of phenylvaleric acid, 0.3% of a mineral solution, and 1.2% of agar powder was sterilized in an autoclave and cooled to 50° C. Thereafter, 0.1% of a DMSO solution containing 0.5% Nile Red was added to the medium. The resultant medium was dispensed in a sterilized Petri dish in an amount of 15 ml per dish and the agar was allowed to solidify to form an agar medium. The compositions of the M9 medium and of the mineral solution were as shown below.

[M9 Medium]

$Na_2HPO_4$: 6.2 g, $KH_2PO_4$: 3.0 g, NaCl: 0.5 g, $NH_4Cl$: 1.0 g (in 1 liter of medium, pH7.0)

[Mineral Solution]

Nitrilotriacetic acid: 1.5 g, $MgSO_4$: 3.0 g, $MnSO_4$: 0.5 g, NaCl: 1.0 g, $FeSO_4$: 0.1 g, $CaCl_2$: 0.1 g, $CoCl_2$: 0.1 g, $ZnSO_4$: 0.1 g, $CuSO_4$: 0.1 g, $AlK(SO_4)_2$: 0.1 g, $H_3BO_3$: 0.1 g, $Na_2MoO_4$: 0.1 g, $NiCl_2$: 0.1 g (in 1 liter, pH 7.0).

Then, 5 g of a soil sample extracted in the field was added to 10 ml of sterilized distilled water and stirred for 1 minute. 0.5 ml of the obtained soil suspension was added to 4.5 ml of sterilized water and stirred to prepare a 10 fold dilution. By repeating similar operations, a 100-fold dilution, a 1,000-fold dilution, and a 10,000-fold dilution were prepared. 0.1 ml each of the 10-fold to 10,000-fold dilutions was dispensed to the previously prepared agar medium and spread over the surface of the agar uniformly. The thus obtained agar medium was transferred to an incubator and cultured at 30° C. for 5 days. After completion of the culture, among red colonies that were considered to have synthesized PHAs, strains having different morphologies were separated. In this manner, over ten wild strains were procured.

Then, each of the above-mentioned wild strains was inoculated from the preservation agar medium in 50 ml of M9 medium (pH 7.0) containing 0.5% of polypeptone, 0.5% of glucose, 0.1% of phenylvaleric acid, and 0.3% of a mineral solution, and cultured with shaking in a 500-ml Sakaguchi flask at 30° C. and 125 strokes/min. Further, culture was similarly performed with respect to the media obtained by adjusting the above-mentioned medium to pH 5.0 and pH 8.5, respectively.

After 72 hours, the cells were recovered by centrifugation and washed with cold methanol and then vacuum dried. The dry cell pellets were suspended in 10 ml of ethyl acetate and stirred at 35° C. for 15 hours to extract PHA. After the extracted solution was filtered through a membrane filter with a pore diameter of 0.45 µm, it was concentrated using a rotary evaporator. The concentrate was added to cold methanol to reprecipitate PHA. Only the precipitates were recovered and vacuum dried. The obtained PHA was weighed to obtain polymer dry weights (PDW). The monomer unit ratio of the obtained PHA was determined with $^1$H-NMR (FT-NMR: Bruker DPX400; resonant frequency: 400 MHz; measured nuclide: $^1$H; solvent used: $CDCl_3$; reference: $TMS/CDCl_3$ encapsulated in a capillary; measuring temperature: room temperature). With the procedure as described above, the obtained polymer dry weight (PDW) and monomer unit ratio were compared to those of respective wild stains and conventional strains to obtain novel strains (strains AG32, KF767, TM90, TM109, and YN21) of the present invention. Further, the YN21 strain was mutated and a microorganism with a further increased PHA productivity was isolated and named YN21M strain.

Example 1

In a 500-ml shaking flask were charged an inorganic medium containing 8.86 g/l disodium hydrogen phosphate, 0.45 g/l potassium dihydrogen phosphate, 1.0 g/l ammonium chloride, 0.5 g/l sodium chloride, and 3 ml/l trace components solution and 50 ml of a medium having a composition of 0.5 g/l polypeptone (Nihon Pharmaceutical Co., Ltd.), and 0.5 g/l D-glucose. 5-Phenylvaleric acid, i.e. an alkanoate, as a substrate and 5-(4-vinylphenyl) valeric acid were added to the resultant in concentrations of 12 mM and 1.5 mM, respectively. The obtained mixture was sterilized at high temperature and high pressure and cooled to room temperature to prepare a medium. The medium had a pH of 7.2.

YN21M strain, one of the novel microorganisms of the present invention, was inoculated in this shaking flask and cultured with shaking at 30° C. at 125 strokes/min. After 40 hours, the cells were recovered by centrifugation and washed with cold methanol, followed by vacuum drying.

The dry cell pellet was suspended in 10 ml of ethyl acetate and stirred at 35° C. for 15 hours to extract PHA. After the extracted solution was filtered through a membrane filter with a pore diameter of 0.45 µm, it was concentrated using a rotary evaporator. The concentrate was added to cold methanol to reprecipitate. PHA. Only the precipitates were recovered and vacuum dried. The obtained PHA was weighed to obtain polymer dry weights (PDW). The monomer unit ratio of the obtained PHA was obtained by $^1$H-NMR(FT-NMR: Bruker DPX400; resonant frequency: 400 MHz; measured nuclide: $^1$H; solvent used: $CDCl_3$; reference: $TMS/CDCl_3$ encapsulated in a capillary; measuring temperature: room temperature). The results of polymer dry weight (PDW) and monomer unit ratio are shown in Table 1.

Comparative Example 1

The experiments were performed in the same manner as that in Example 1 except that in stead of the YN21M strain used in Example 1, each strain out of *Pseudomonas* sp.

YN21 (FERM BP-8569), *Pseudomonas cichorii* YN2 (FERM BP-7375), *Pseudomonas cichorii* H45 (FERM BP-7374), *Pseudomonas jessenii* P161 (FERM BP-7376), and *Pseudomonas putida* P91 (FERM7 BP-7373) was, separately used. The results of polymer dry weight (PDW) and monomer unit ratio for each strain are shown in Table 1.

TABLE 1

|  |  |  | Monomer unit ratio (mol %) |  |
|---|---|---|---|---|
|  | Strain | PDW (g/L) | 3HPV | 3HVPV |
| Example 1 | YN21M | 1.55 | 91.8 | 7.5 |
| Comparative | YN21 | 0.91 | 90.6 | 8.3 |
| Example 1 | YN2 | 1.24 | 91.5 | 8.1 |
|  | H45 | 0.59 | 89.4 | 8.7 |
|  | P161 | 0.65 | 90.5 | 7.6 |
|  | P91 | 0.14 | 90.9 | 8.4 |

PDW: Polymer dry weight
3HPV: 3-Hydroxy-5-phenylvalerate unit
3HVPV: 3-Hydroxy-5-(4-vinylphenyl) valerate unit The results of Example 1 and each Comparative Examples shown in Table 1 indicate that PDW of Example 1 was higher than any of the PDWs of Comparative Example 1. This shows that with the substrate and under the culture conditions mentioned above, the YN21M strain had a higher PHA productivity than those of the strains YN21, YN2, H45, P161, and P91.

Example 2

In a 500-ml shaking flask were charged an inorganic medium containing 6.2 g/l disodium hydrogen phosphate, 3 g/l potassium dihydrogen phosphate, 1.0 g/l ammonium chloride, 0.5 g/l sodium chloride, and 3 ml/l trace components solution and 50 ml of a medium having a composition of 0.5 g/l polypeptone (Nihon Pharmaceutical Co., Ltd.), and 0.5 g/l D-glucose. Further, a defoaming agent "ANTI-FOAM PE-M" (manufactured by WAKO Pure Chemical Industries, Ltd.) as a dispersant for the substrate was added to the resultant composition in a concentration of 0.5 ml/l. After the obtained mixture was sterilized at high temperature and high pressure and cooled to room temperature, n-amyl-benzene, i.e. an alkane, as a substrate, was added thereto in a concentration of 6 mM to prepare a medium. The medium had a pH of 7.0. *Pseudomonas* sp. YN21M of the present invention was inoculated in this shaking flask and cultured with shaking at 30° C. at 125 strokes/mm. After 40 hours, the cells were recovered by centrifugation and PHA was extracted in the same manner as that in Example 1 and the obtained PHA was weighed to obtain polymer dry weights (PDW: g/l). Further, the monomer unit ratio of the obtained PHA was determined by $^1$H-NMR in the same manner as that in Example 1. The results of polymer dry weight (PDW) and monomer unit ratio are shown in Table 2.

Comparative Example 2

The experiments were performed in the same manner as that in Example 2 except that in stead of the YN21M strain used in Example 2, each strain out of YN21, YN2, H45, P161, and P91 used in Comparative Example 1 was separately used. The results of polymer dry weight (PDW) and monomer unit ratio for each strain are shown in Table 2.

TABLE 2

|  |  |  | Monomer unit ratio (mol %) |
|---|---|---|---|
|  | Strain | PDW (g/L) | 3HPV |
| Example 2 | YN21M | 0.52 | 95.2 |
| Comparative | YN21 | 0.15 | 94.3 |
| Example 2 | YN2 | 0.17 | 94.8 |
|  | H45 | 0.08 | 91.2 |
|  | P161 | 0.12 | 93.5 |
|  | P91 | 0.03 | 87.6 |

PDW: Polymer dry weight
3HPV: 3-Hydroxy-5-phenylvalerate unit

The results of Example 2 and each Comparative Examples shown in Table 2 indicate that PDW of Example 2 was higher than any of the PDWs of Comparative Example 2. This shows that with the substrate and under the culture conditions mentioned above, the YN21M strain had a higher PHA productivity than those of the strains YN21, YN2, H45, P161, and P91.

Example 3

The experiments were performed in the same manner as that in Example 2 except that in stead of ANTIFOAM PE-M, the defoaming agent used as a dispersant in Example 2, Tween 20 (manufactured by Kishida Chemical Co. Ltd.), COLORIN 102, a defoaming agent (manufactured by Sanyo Chemical Industries, Ltd.), ADEKANOL LG-126, a defoaming agent (manufactured by Asahi Denka Co., Ltd.), or DISFOAM C-118, a defoaming agent (manufactured by NOF Corporation) was separately used as a dispersant. The media had a pH of 7.0. The results of polymer dry weight (PDW) and monomer unit ratio in each dispersant are shown in Table 3 together with the results of Example 2.

Comparative Example 3

The experiments were performed in the same manner as that in Example 2 except that neither ANTIFOAM PE-M, the defoaming agent used as a dispersant in Example 2, nor any dispersant was used. The results of polymer dry weight (PDW) and monomer unit ratio are shown in Table 3.

TABLE 3

|  |  |  | Monomer unit ratio (mol %) |
|---|---|---|---|
|  | Dispersant | PDW (g/L) | 3HPV |
| Example 2 | Antiform PE-M | 0.48 | 94.4 |
| Example 3 | Tween20 | 0.46 | 89.0 |
|  | COLORIN 102 | 0.46 | 93.7 |
|  | ADEKANOL LG-126 | 0.46 | 93.1 |
|  | DISFOAM | 0.45 | 95.0 |
| Comparative Example 3 | None | 0.15 | 91.5 |

PDW: Polymer dry weight
3HPV: 3-Hydroxy-5-phenylvalerate unit

The results of Examples 2 and 3 and Comparative Example 3 shown in Table 3 indicate that PDWs of Examples 2 and 3 were higher than that of Comparative Example 3. This shows that with the substrate and under the culture conditions mentioned above, use of surfactants or defoaming agent as dispersants led to improved PHA productivity.

Example 4

In a 500-ml shaking flask was charged 50 ml of a medium having the same composition as that of the medium used in Example 2 and 5-phenoxyvaleric acid, as a substrate, was added thereto so as to make a concentration of 6 mM. The resultant mixture was sterilized at high temperature and high pressure, and then cooled to room temperature to prepare a medium. The medium had a pH of 7.0. *Pseudomonas* sp. TM109, one of the novel microorganisms of the present invention, was inoculated in this shaking flask and cultured with shaking at 30° C. at 125 strokes/min. After 40 hours, the cells were recovered by centrifugation and PHA was extracted in the same manner as that in Example 1 and the obtained PHA was weighed. Further, the monomer unit ratio of the obtained PHA was determined by $^1$H-NMR in the same manner as that in Example 1. The results of polymer dry weight (PDW) and monomer unit ratio are shown in Table 4.

Comparative Example 4

The experiments were performed in the same manner as that in Example 4 except that in stead of the TM109 strain used in Example 4, each strain out of YN21, YN2, H45, P161, and P91 used in Comparative Example 1 was separately used. The results of polymer dry weight (PDW) and monomer unit ratio for each strain are shown in Table 4.

TABLE 4

| | Strain | PDW (g/L) | Monomer unit ratio (mol %) 3HP$_x$V |
|---|---|---|---|
| Example 4 | TM109 | 0.83 | 98.8 |
| Comparative Example 4 | YN21 | 0.21 | 98.6 |
| | YN2 | 0.22 | 99.1 |
| | H45 | 0.10 | 97.6 |
| | P161 | 0.15 | 98.3 |
| | P91 | 0.02 | 95.2 |

PDW: Polymer dry weight
3HPxV: 3-Hydroxy-5-phenoxyvalerate unit

The results of Example 4 and each Comparative Examples shown in Table 4 indicate that PDW of Example 4 was higher than any of the PDWs of Comparative Example 4. This shows that with the substrate and under the culture conditions mentioned above, the TM109M strain had a higher PHA productivity than those of the strains YN21, YN2, H45, P161, and P91.

Example 5

5-Phenylvaleric acid, as a substrate, was added to a medium having the same composition as that of the medium used in Example 2 so as to make a concentration of 6 mM. The resultant mixture was sterilized at high temperature and high pressure, and then cooled to room temperature to prepare a medium. Then the pH of aliquots of the medium were each adjusted to pH 5.0, 5.5, 6.0, 6.5, and 7.0, respectively, and the resultant media were subjected to filtration sterilization. 50 ml of each medium thus obtained was charged in a 500-ml shaking flask. Thereafter, *Pseudomonas* sp. KF767, one of the novel microorganisms of the present invention, was inoculated in this shaking flask and cultured with shaking at 30° C. at 125 strokes/min. After 62 hours, the cells were recovered by centrifugation and PHA was extracted in the same manner as that in Example 1 and the obtained PHA was weighed. Further, the monomer unit ratio of the obtained PHA was determined by $^1$H-NMR in the same manner as that in Example 1. The results of polymer dry weight (PDW) and monomer unit ratio are shown in Table 5.

Comparative Example 5

The experiments were performed in the same manner as that in Example 5 except that in stead of the KF767 strain used in Example 5, the YN2 strain used in Comparative Example 1 was used. The results of polymer dry weight (PDW) and monomer unit ratio for each strain are shown in Table 5. Further, experiments were performed in the same manner as that in Example 5 except that among the various media used in the experiments in Example 5, only the medium adjusted to pH 5.0 was used and that in stead of the KF767 strain, each strain out of YN21, H45, P161, and P91 used in Comparative Example 1 was separately used. The results of polymer dry weight (PDW) and monomer unit ratio for each strain are shown in Table 5.

TABLE 5

| | Strain | pH | PDW (g/L) | Monomer unit ratio (mol %) 3HPV |
|---|---|---|---|---|
| Example 5 | KF767 | 5.0 | 0.77 | 94.5 |
| | | 5.5 | 0.72 | 97.3 |
| | | 6.0 | 0.69 | 98.4 |
| | | 6.5 | 0.76 | 97.7 |
| | | 7.0 | 0.74 | 96.2 |
| Comparative Example 5 | YN2 | 5.0 | 0.29 | 92.2 |
| | | 5.5 | 0.41 | 94.7 |
| | | 6.0 | 0.49 | 96.4 |
| | | 6.5 | 0.58 | 97.7 |
| | | 7.0 | 0.78 | 98.5 |
| | YN21 | 5.0 | 0.25 | 91.3 |
| | H45 | 5.0 | 0 | — |
| | P161 | 5.0 | 0.21 | 92.7 |
| | P91 | 5.0 | 0.08 | 91.2 |

PDW: Polymer dry weight
3HPV: 3-Hydroxy-5-phenylvalerate unit

The results of Example 5 and Comparative Example 5 shown in Table 5 indicate that the PDWs of Example 5 at pH 5.0, 5.5, 6.0, and 6.5, respectively, were higher than any of the PDWs of Comparative Example 5 at pH 5.0, 5.5, 6.0, and 6.5, respectively, and were relatively stable at pH 5.0 to 7.0. This shows that with the substrate and under the culture conditions mentioned above, the KF767 strain had a higher PHA productivity than those of the strains YN21, YN2, H45, P161, and P91 and could stably produce PHA in acidic media.

Example 6

5-Phenylvaleric acid, as a substrate, was added to a medium having the same composition as that of the medium used in Example 2 so as to make a concentration of 18 mM. The resultant mixture was sterilized at high temperature and high pressure, and then cooled to room temperature to prepare a medium. Then the pH of aliquots of the medium were each adjusted to pH 8.5, 8.0, 7.5, and 7.0, respectively, and the resultant media were subjected to filtration sterilization. 50 ml of each medium thus obtained was charged in a 500 ml shaking flask. Thereafter, *Pseudomonas* sp AG32 or TM90 of the novel microorganisms of the present invention, was inoculated in this shaking flask separately and cultured with shaking at 30° C. at 125 strokes/min. After 40 hours, the cells were recovered by centrifugation and PHA was extracted in the same manner as that in Example 1 and the obtained PHA was weighed. Further, the monomer unit ratio of the obtained PHA was determined by $^1$H-NMR in the same manner as that in Example 1. The results of polymer dry weight (PDW) and monomer unit ratio are shown in Table 6.

Comparative Example 6

The experiments were performed in the same manner as that in Example 6 except that in stead of the AG32 or TM90 strain used in Example 6, the YN2 strain used in Comparative Example 1 was used. The results of polymer dry weight (PDW) and monomer unit ratio for each strain are shown in Table 5. Further, experiments were performed in the same manner as that in Example 6 except that among the various media used in the experiments in Example 6 only the medium adjusted to pH 8.0 was used and that in stead of the AG32 or TM90 strain, each strain out of YN21, H45, P161, and P91 used in Comparative Example 1 was separately used. The results of polymer dry weight (PDW) and monomer unit ratio for each strain are shown in Table 6.

TABLE 6

| | Strain | pH | PDW (g/L) | Monomer unit ratio (mol %) 3HPV |
|---|---|---|---|---|
| Example 6 | AG32 | 8.5 | 0.21 | 92.5 |
| | | 8.0 | 0.52 | 97.4 |
| | | 7.5 | 0.58 | 98.2 |
| | | 7.0 | 0.63 | 98.7 |
| | TM90 | 8.5 | 0.15 | 93.2 |
| | | 8.0 | 0.50 | 97.2 |
| | | 7.5 | 0.66 | 98.7 |
| | | 7.0 | 0.81 | 99.4 |
| Comparative Example 6 | YN2 | 8.5 | 0 | — |
| | | 8.0 | 0.01 | 90.5 |
| | | 7.5 | 0.54 | 97.3 |
| | | 7.0 | 0.78 | 98.7 |
| | YN21 | 8.0 | 0.01 | 91.4 |
| | H45 | 8.0 | 0 | — |
| | P161 | 8.0 | 0.06 | 96.7 |
| | P91 | 8.0 | 0.01 | 91.2 |

PDW: Polymer dry weight
3HPV: 3-Hydroxy-5-phenylvalerate unit

The results of Example 6 and Comparative Example 6 shown in Table 6 indicate that the PDWs of Example 6 at pH 8.5, 8.0, and 7.5, respectively, were higher than any of the PDWs of Comparative Example 6 at pH 8.5, 8.0, and 7.5, respectively, and were relatively stable at pH 8.5 to 7.0. This shows that with the substrate and under the culture conditions mentioned above, the AG32 or TM90 strain had a higher PHA productivity than those of the strains YN21, YN2, H45, P161, and P91 and could stably produce PHA in basic media.

Example 7

In a 500-ml shaking flask was charged 50 ml of a medium having the same composition as that of the medium used in Example 2 and ANTIFOAM PE-M was added thereto in the same manner as that in Example 2 in a concentration of 0.5 ml/l. The resultant mixture was sterilized at high temperature and high pressure, and then cooled to room temperature to prepare a medium. Thereafter, amyl phenyl ether, i.e. an alkane, was added thereto as a substrate so as to make a concentration of 6 mM. YN21M strain, one of the novel microorganisms of the present invention, was inoculated in this shaking flask and cultured with shaking at 30° C. at 125 strokes/min. After 40 hours, the cells were recovered by centrifugation and PHA was extracted in the same manner as that in Example 1 and the obtained PHA was weighed. As a result, the polymer dry weight (PDW) was 0.20 g/l. Further, the structure determination of the obtained PHA by $^1$H-NMR in the same manner as that in Example 1 gave a monomer unit ratio of 3-hydroxy-5-phenoxyvaleric acid of 94.8 mol %. From the above, it was confirmed that PHA with a 3-hydroxy-5-phenoxyvalerate unit could be synthesized from amyl phenyl ether by the YN21M strain.

Example 8

In a 500-ml shaking flask were charged an inorganic medium containing 6.2 g/l disodium hydrogen phosphate, 3 g/l potassium dihydrogen phosphate, 1.0 g/l ammonium chloride, 0.5 g/l sodium chloride, and 3 ml/l trace components solution and 50 ml of a medium having a composition of 1.0 g/l polypeptone (Nihon Pharmaceutical Co., Ltd.), and 1.0 g/l D-glucose. ANTIFOAM PE-M was added to the resultant mixture in the same manner as in Example 2 in a concentration of 0.5 ml/l. The obtained mixture was sterilized at high temperature and high pressure and cooled to room temperature to prepare a medium. Thereafter, n-amylbenzene, i.e. an alkane, was added thereto as a substrate so as to make a concentration of 6 mM. Also, 5-(vinylphenyl) pentane, i.e. an alkane, was further added thereto so as to make a concentration of 0.8 mM. YN21M strain, one of the novel microorganisms of the present invention, was inoculated in this shaking flask and cultured with shaking at 30° C. at 125 strokes/min. After 40 hours, the cells were recovered by centrifugation and PHA was extracted in the same manner as that in Example 1 and the obtained PHA was weighed. As a result, the polymer dry weight (PDW) was found to be 0.72 g/l. Further, the structure determination of the obtained PHA by $^1$H-NMR in the same manner as that in Example 1 gave a monomer unit ratio of 3-hydroxy-5-phenylvaleric acid of 80.7 mol %. Also, the monomer unit ratio of 3-hydroxy-5-(4-vinylphenyl) valeric acid was found to be 15.3 mol %. From the above, it was confirmed that PHA including a 3-hydroxy-5-phenylvalerate unit and 3-hydroxy-5-(4-vinylphenyl) valerate unit could be synthesized from n-amylbenzene and vinylphenylpentane by the YN21M strain.

Example 9

In a 500-ml shaking flask was charged 50 ml of a medium having the same composition as that of the medium used in Example 2 and ANTIFOAM PE-M was added thereto in the same manner as that in Example 2 in a concentration of 0.5 ml/l. The resultant mixture was sterilized at high temperature and high pressure, and then cooled to room temperature to prepare a medium. Thereafter, n-amylbenzene, i.e. an alkane, was added thereto as a substrate so as to make a concentration of 9 mM. Also, 10-undecenoic acid, i.e. an alkanoate having unsaturation in the terminal, was added thereto so as to make a concentration of 2.25 mM. A *Pseudomonas* sp. YN21M strain, one of the novel microorganisms of the present invention, was inoculated in this shaking flask and cultured with shaking at 30° C. at 125 strokes/min. After 40 hours, the cells were recovered by centrifugation and PHA was extracted in the same manner as that in Example 1 and the obtained PHA was weighed. As a result, the polymer dry weight (PDW) was found to be 0.78 g/l. Further, the structure determination of the obtained PHA by $^1$H-NMR in the same manner as that in Example 1 gave a monomer unit ratio of 3-hydroxy-5-phenylvaleric acid of 56.7 mol % and the monomer unit ratio of 3-hydroxy-5-(4-vinylphenyl)valeric acid unit was found to be 36.3 mol %. From the above, it was confirmed that PHA with a 3-hydroxy-5-phenylvalerate unit and a 3-hydroxy-10-undecenoate unit could be synthesized from n-amylbenzene and 10-undecenoic acid by the YN21M strain.

Example 10

In a 2-liter shaking flask was charged 500 ml of a medium having the same composition as that of the medium used in Example 2 and 5-phenylvaleric acid and 5-(4-vinylphenyl) valeric acid, i.e. alkanoates, were added thereto as substrates so as to make concentrations of 12 mM and 2.125 mM, respectively. The resultant mixture was sterilized at high temperature and high pressure, and then cooled to room temperature to prepare a medium.

Similarly, 5 liters of a medium having the same composition as that of the medium used in Example 2 was charged in a pressure-resistant bottle and 5-phenylvaleric acid and 5-(4-vinylphenyl) valeric acid, i.e. alkanoates, as substrates so as to make concentrations of 12 mM and 2.125 mM, respectively. The resultant mixture was sterilized at high temperature and high pressure, and then cooled to room temperature to prepare a medium. A *Pseudomonas* sp. YN21M strain, one of the novel microorganisms of the present invention, was inoculated in the above-mentioned shaking flask and cultured with shaking at 30° C. at 125 strokes/min. After 8 hours, the culture broth was introduced into a sterilized chemostat (BMJ-01, manufactured by Able Co. Ltd.) and a continuous culture was performed using the medium contained in the above-mentioned pressure-resistant bottle by means of a microtube pump. In this case, the amount of the medium was 500 ml, the flow rate was 50 ml/hr, aeration rate was 1 liter/min, agitation rate was 300 rpm, and the temperature was 30° C.

After 64 hours, 50 ml of a discharged culture broth was collected and cells were recovered by centrifugation. Then, PHA was extracted in the same manner as that in Example 1 and the obtained PHA was weighed. As a result, the polymer dry weight (PDW) was found to be 0.89 g/l. Further, the structure determination of the obtained, PHA by $^1$H-NMR in the same manner as that in Example 1 gave a monomer unit ratio of 3-hydroxy-5-phenylvaleric acid of 91.7 mol % and the monomer unit ratio of 3-hydroxy-5-(4-vinylphenyl)valerate unit was found to be 7.3 mol %. Then, while maintaining the aeration, agitation, and, temperature control, flow of the medium into the chemostat was stopped to shift from the continuous culture to batch culture. After 40 hours, 50 ml of the culture broth was collected from the culture tank, and cells were recovered by centrifugation. PHA was extracted in the same manner as that in Example 1 and the obtained PHA was weighed. As a result, the polymer dry weight (PDW) was found to be 2.11 g/l. Further, the structure determination of the obtained PHA by $^1$H-NMR in the same manner as that in Example 1 gave a monomer unit ratio of 3-hydroxy-5-phenylvalerate of 91.2 mol % and the monomer unit ratio of 3-hydroxy-5-(4-vinylphenyl)valeric acid was found to be 7.5 mol %. From the above, it was confirmed that by the continuous culturing or by a culture method that includes culturing by a combination of continuous culturing and batch culturing, PHA with a 3-hydroxy-5-phenylvaleric acid unit and a 3-hydroxy-5-(4-vinylphenyl)valerate unit could be synthesized from amylbenzene and 3-hydroxy-5-(4-vinylphenyl)valeric acid by the YN21M strain.

This application claims priority from Japanese Patent Application No. 2005-023977 filed on Jan. 31, 2005, which is hereby incorporated by reference herein.

What is claimed is:

1. A biologically pure culture of a microorganism selected from the group consisting of *Pseudomonas* sp. AG32 strain (FERM BP-8586), *Pseudomonas* sp. KF767 strain (FERM BP-8589), *Pseudomonas* sp. TM90 strain (FERM BP-8587), *Pseudomonas* sp. TM109 strain (FERM BP-8588), and *Pseudomonas* sp. YN21M strain (FERM BP-8585), which is capable of synthesizing a polyhydroxyalkanoate containing, in a polymer molecule thereof, at least one unit selected from the group consisting of units represented by formulae (1) to (4):

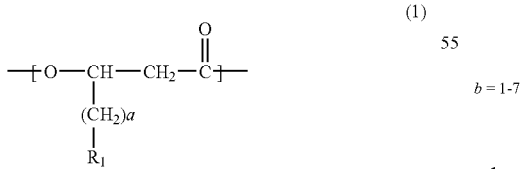

$a = 1-8$ wherein a is an integer selected from the range shown in the formula; $R_1$ represents at least one residue represented by any one of formulae (5) to (12); provided that when a plurality of units represented by formula (1) are present, each unit independently has the meaning defined above;

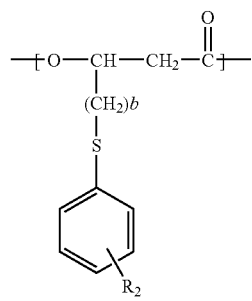

$b = 1-7$ wherein $R_2$ represents a substituent to the aromatic ring and represents a hydrogen atom, a halogen atom, a CN group, an $NO_2$ group, COOR' where R' represents any one of H, Na, K, $CH_3$ and $C_2H_5$, $SO_2R''$ where R'' represents any one of OH, ONa, OK, a halogen atom, $OCH_3$ and $OC_2H_5$, a $CH_3$ group, a $C_2H_5$ group, a $C_3H_7$ group, a $(CH_3)_2$—CH group or a $(CH_3)_3$—C group; b is an integer selected from the range shown in the formula, provided that when a plurality of units represented by formula (2) are present, each unit independently has the meaning defined above;

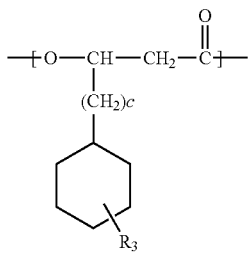
(3)

$c = 0\text{-}8$ wherein $R_3$ represents a substituent to the cyclohexyl group and represents a hydrogen atom, a CN group, an $NO_2$ group, a halogen atom, a $CH_3$ group, a $C_2H_5$ group, a $C_3H_7$ group, a $CF_3$ group, a $C_2F_5$ group or a $C_3F_7$ group; c is an integer selected from the range shown in the formula, provided that when a plurality of units represented by formula (3) are present, each unit independently has the meaning defined above;

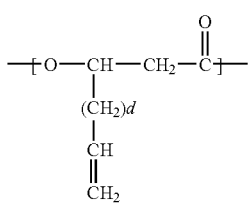
(3)

$d = 1\text{-}8$ wherein d is an integer selected from the range shown in the formula, provided that when a plurality of units represented by formula (4) are present, each unit independently has the meaning defined above;

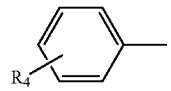
(5)

wherein $R_4$ represents a substituent to the aromatic ring; $R_4$ represents a hydrogen atom, a halogen atom, a CN group, an $NO_2$ group, a $CH_3$ group, a $C_2F_5$ group, a $C_3H_7$ group, a $CH=CH_2$ group, a $CF_3$ group, a $C_2H_5$ group, or a $C_3F_7$ group, provided that when a plurality of units are present, each unit independently has the meaning defined above;

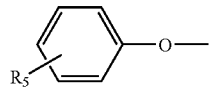
(6)

wherein $R_5$ represents a substituent to the aromatic ring; $R_5$ represents a hydrogen atom, a halogen atom, a CN group, an $NO_2$ group, a $CH_3$ group, a $C_2H_5$ group, a $C_3H_7$ group, an $SCH_3$ group, a $CF_3$ group, a $C_2F_5$ group, or a $C_3F_7$ group, provided that when a plurality of units are present, each unit independently has the meaning defined above;

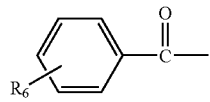
(7)

wherein $R_6$ represents a substituent to the aromatic ring; $R_6$ represents a hydrogen atom, a halogen atom, a CN group, an $NO_2$ group, a $CH_3$ group, a $C_2H_5$ group, a $C_3H_7$ group, a $CF_3$ group, a $C_2F_5$ group, or a $C_3F_7$ group, provided that when a plurality of units are present, each unit independently has the meaning defined above;

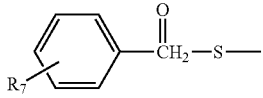
(8)

wherein $R_7$ represents a substituent to the aromatic ring and represents a hydrogen atom, a halogen atom, a CN group, an $NO_2$ group, COOR' where R' represents any one of H, Na, K, $CH_3$ and $C_2H_5$, $SO_2R''$ where R" represents any one of OH, ONa, OK, a halogen atom, $OCH_3$ and $OC_2H_5$), a $CH_3$ group, a $C_2H_5$ group, a $C_3H_7$ group, a $(CH_3)_2$—CH group or a ($-CH_3)_3$—C group, provided that when a plurality of units are present, each unit independently has the meaning defined above;

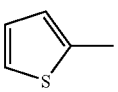
(9)

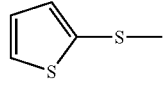
(10)

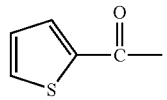
(11)

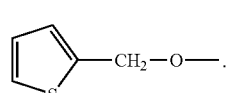
(12)

* * * * *

UNITED STATES PATENT AND TRADEMARK OFFICE
CERTIFICATE OF CORRECTION

PATENT NO. : 7,267,974 B2
APPLICATION NO. : 11/340728
DATED : September 11, 2007
INVENTOR(S) : Kozaki et al.

It is certified that error appears in the above-identified patent and that said Letters Patent is hereby corrected as shown below:

COLUMN 1:
Line 36, "them" should read -- those --;
Line 43, "P91-strain" should read -- P91strain --; and
Line 60, "their production" should read -- the production --.

COLUMN 2:
Line 8, "higher-productivity" should read -- higher productivity --; and
Line 16, "In particular" should read -- In particular, --.

COLUMN 5:
Line 17, "a $CH_3$ group," should read -- a $CH_3$ group, a $C_2H_5$ group, --; and
Line 33, "$OC_2H_5$)," should read -- $OC_2H_5$, --.

COLUMN 6:
Line 52, "none." should read -- none --; and
Line 65, "Gelatin-hydrolysis: –" should read -- Gelatin hydrolysis: – --.

COLUMN 7:
Line 15, "3) Substrate Assimilabilities" should read -- 3) Substrate-Assimilation Abilities --.

COLUMN 8:
Line 29, "Q/F test:" should read -- O/F test: --; and
Line 36, "40 C.°: –" should read -- 40° C.: – --.

COLUMN 9:
Line 36, "40 C.°: –" should read -- 40° C.: – --.

COLUMN 10:
Line 47, "40°0 C.: –" should read -- 40° C.: – --.

COLUMN 11:
Line 29, "on-King's" should read -- on King's --;
Line 31, "40 C.°: –" should read -- 40° C.: – --;
Line 41, "Abilities." should read -- Abilities --; and
Line 64, "Plopylene" should read -- Propylene --.

UNITED STATES PATENT AND TRADEMARK OFFICE
CERTIFICATE OF CORRECTION

PATENT NO. : 7,267,974 B2
APPLICATION NO. : 11/340728
DATED : September 11, 2007
INVENTOR(S) : Kozaki et al.

It is certified that error appears in the above-identified patent and that said Letters Patent is hereby corrected as shown below:

COLUMN 13:
Line 19, "an thienyl" should read -- a thienyl --; and
Line 53, "$C_3F_7$;" should read -- $C_3F_7$ group; --.

COLUMN 14:
Line 1, "structures that," should read -- structures that --.

COLUMN 16:
Line 19, "ganism of" should read -- ganisms of --.

COLUMN 17:
Line 50, "10 fold" should read -- 10-fold --.

COLUMN 18:
Line 66, "in stead" should read -- instead --.

COLUMN 19:
Line 22, "each" should read -- each of the --; and
Line 63, "in stead" should read -- instead --.

COLUMN 20:
Line 14, "each" should read -- each of the --; and
Line 26, "in stead" should read -- instead --.

COLUMN 21:
Line 24, "in stead" should read -- instead --; and
Line 42, "each" should read -- each of the --.

COLUMN 22:
Line 9, "in stead" should read -- instead --; and
Line 16, "in stead" should read -- instead --.

COLUMN 23:
Line 11, "in stead" should read -- instead --; and
Line 18, "in stead" should read -- instead --.

COLUMN 31:
Line 34, "(3)" should read -- (4) --.

UNITED STATES PATENT AND TRADEMARK OFFICE
CERTIFICATE OF CORRECTION

PATENT NO.       : 7,267,974 B2
APPLICATION NO.  : 11/340728
DATED            : September 11, 2007
INVENTOR(S)      : Kozaki et al.

It is certified that error appears in the above-identified patent and that said Letters Patent is hereby corrected as shown below:

COLUMN 32:
Line 40, "$OC_2H_5$)," should read -- $OC_2H_5$, --; and
Line 42, "$(-CH_3)_3-C$" should read -- $(CH_3)_3-C$ --.

Signed and Sealed this

Twentieth Day of May, 2008

JON W. DUDAS
*Director of the United States Patent and Trademark Office*

SEQUENCE LISTING

```
<160> NUMBER OF SEQ ID NOS: 3

<210> SEQ ID NO 1
<211> LENGTH: 1461
<212> TYPE: DNA
<213> ORGANISM: Pseudomonas sp. KF767
<220> FEATURE:
<223> OTHER INFORMATION: Partial 16S DNA sequence

<400> SEQUENCE: 1
ctggcggcag gcctaacaca tgcaagtcga gcggatgaag agagcttgct ctctgattca       60
gcggcggacg ggtgagtaat gcctaggaat ctgcctggta gtgggggaca acgtttcgaa      120
aggaacgcta ataccgcata cgtcctacgg gagaaagcag gggaccttcg ggccttgcgc      180
tatcagatga gcctaggtcg gattagctag ttggtgaggt aatggctcac caaggcgacg      240
atccgtaact ggtctgagag gatgatcagt cacactggaa ctgagacacg gtccagactc      300
ctacgggagg cagcagtggg gaatattgga caatgggcga aagcctgatc cagccatgcc      360
gcgtgtgtga agaaggtctt cggattgtaa agcactttaa gttgggagga agggcagtag      420
```

```
attaatactc tgctgttttg acgttaccga cagaataagc accggctaac tctgtgccag        480
cagccgcggt aatacagagg gtgcaagcgt taatcggaat tactgggcgt aaagcgcgcg        540
taggtggttt gttaagttgg atgtgaaagc cccgggctca acctgggaac tgcattcaaa        600
actgacaagc tagagtatgg tagagggtgg tggaatttcc tgtgtagcgg tgaaatgcgt        660
agatatagga aggaacacca gtggcgaagg cgaccacctg gactgatact gacactgagg        720
tgcgaaagcg tggggagcaa acaggattag ataccctggt agtccacgcc gtaaacgatg        780
tcaactagcc gttgggagcc ttgagctctt agtggcgcag ctaacgcatt aagttgaccg        840
cctggggagt acggccgcaa ggttaaaact caaatgaatt gacgggggcc cgcacaagcg        900
gtggagcatg tggtttaatt cgaagcaacg cgaagaacct taccaggcct tgacatccaa        960
tgaactttcc agagatggat tggtgccttc gggaacattg agacaggtgc tgcatggctg       1020
tcgtcagctc gtgtcgtgag atgttgggtt aagtcccgta acgagcgcaa cccttgtcct       1080
tagttaccag cacgtaatgg tgggcactct aaggagactg ccggtgacaa accggaggaa       1140
ggtggggatg acgtcaagtc atcatggccc ttacggcctg ggctacacac gtgctacaat       1200
ggtcggtaca gagggttgcc aagccgcgag gtggagctaa tcccataaaa ccgatcgtag       1260
tccggatcgc agtctgcaac tcgactgcgt gaagtcggaa tcgctagtaa tcgcgaatca       1320
gaatgtcgcg gtgaatacgt tcccgggcct tgtacacacc gcccgtcaca ccatgggagt       1380
gggttgcacc agaagtagct agtctaacct tcgggggggac ggttaccacg gtgtgattca       1440
tgactggggg aagtcgaaca a                                                  1461

<210> SEQ ID NO 2
<211> LENGTH: 903
<212> TYPE: DNA
<213> ORGANISM: Pseudomonas sp. KF767
<220> FEATURE:
<223> OTHER INFORMATION: Partial gyrB DNA sequence

<400> SEQUENCE: 2
tcctacaagg tatccggcgg cctgcacggc gtaggtgtgt cggtagtgaa cgccctgtct         60
gaagagctag tcctcaccgt tcgccgtagc ggcaagatct gggaacagac ctacgtccat        120
ggtgttccgc aggagccgat gaagatcgtt ggcgacagcg aaaccactgg cacccagatc        180
cacttcaagg cttccagcga aaccttcaag aacatccact tcagctggga catcctggcc        240
aagcggattc gtgaactgtc cttcctcaac tccggtgtcg gtatcgtcct caaggacgag        300
cgcagcggca aggaagagct gttcaagtac gaaggcggct tgcgtgcgtt cgttgaatac        360
ctgaacacca acaagacccc ggtcaaccag gtgttccact tcaacatcca gcgtgaagac        420
ggcattggcg tggaaatcgc cctgcagtgg aacgacagct tcaacgagaa cctgttgtgc        480
ttcaccaaca acattccgca gcgcgatggc ggtactcacc tggtgggttt ccgttccgca        540
ctgacgcgta acctcaacac ctatatcgaa gctgaaggcc tggcgaagaa gcacaaggtc        600
gccaccaccg gtgacgacgc ccgtgaaggc ctgaccgcga tcatttcggt aaaagtgccg        660
gatccgaagt tcagctccca gaccaaggac aagctggtct cttccgaagt gaagaccgcg        720
gtcgaacagg aaatgggcaa gtacttctcc gacttcctgc tggaaaaccc gaacgaagcc        780
aagctggttg tcgcaagat gatcgacgcg gcacgtgctc gtgaagccgc gcgcaaggcc        840
cgtgagatga cccgccgtaa aggcgcactg gacatcgctg gcctgccggg caaactggct        900
gat                                                                      903
```

```
<210> SEQ ID NO 3
<211> LENGTH: 801
<212> TYPE: DNA
<213> ORGANISM: Pseudomonas sp. KF767
<220> FEATURE:
<223> OTHER INFORMATION: Partial rpoD DNA sequence

<400> SEQUENCE: 3
gagctcctca cgcgtgaagg cgaaatcgaa atcgccaagc gtattgaaga gggcatccgt      60
gaagtgatga gcgcaatcgc gcacttccct ggcacggttg atcatattct ctccgaatac     120
actcgcgtca ccaccgaagg tggccgcctg tccgacgtcc tgagcggtta tatcgacccg     180
gacgacggta ttgcgccgcc tgcagcggag gtgccaccgc cgatcgacac caagaccgcg     240
aaagcggatg acgattccga cgacgatgac gccgaagctt ccgatgacga agaagaagcc     300
gaaagcggtc cggatccgat catcgccgcc cagcgctttg gtgctgtcgc cgatcagatg     360
gaaatcaccc gcaaggcgct gaaaaagcac ggtcgccaca acaagctggc gattgccgag     420
ctgttggccc ttgccgacct gttcatgccg atcaaactgg ttccgaagca attcgaaggc     480
ctggtcgagc gtgtgcgcag cgccctggat cgtctgcgtc agcaagagcg tgcaatcatg     540
cagctctgcg ttcgtgatgc acgcatgccg cgtgctgact tcctgcgcca gttcccgggc     600
aacgaagtgg acgaaagctg gagcgatgca ctggccaaag gcaaaagcaa atacgctgaa     660
gccatcggtc gcgtgcagcc ggacatcatt cgctgccagc agaagctgac cgcgctggaa     720
accgaaaccg gtttgacgat cgccgagatc aaggacatca accgtcgcat gtcgatcggt     780
gaggccaagg cccgccgcgc g                                               801
```